United States Patent [19]
Thompson

[11] Patent Number: 5,629,985
[45] Date of Patent: May 13, 1997

[54] APPARATUS AND METHODS FOR AUDITORY CONDITIONING

[76] Inventor: Billie M. Thompson, 1635 E. Seldon La., Phoenix, Ariz. 85020

[21] Appl. No.: 311,215

[22] Filed: Sep. 23, 1994

[51] Int. Cl.$^6$ ........................................... H04R 25/00
[52] U.S. Cl. .................... 381/68.4; 381/68.2; 381/98; 381/103
[58] Field of Search ...................... 381/68.2, 68.4, 381/68, 98, 97, 99–103, 68.3

[56] References Cited

U.S. PATENT DOCUMENTS

| | | | |
|---|---|---|---|
| 4,316,060 | 2/1982 | Adams et al. | 381/98 |
| 4,405,831 | 9/1983 | Michaelson | 381/68.4 |
| 4,661,982 | 4/1987 | Kitazato et al. | 381/98 |
| 4,688,258 | 8/1987 | Kunugi et al. | 381/102 |
| 4,731,850 | 3/1988 | Levitt et al. | 381/68.2 |
| 4,791,672 | 12/1988 | Nunley et al. | 381/68.2 |
| 4,837,832 | 6/1989 | Fanshel | 381/68.4 |
| 5,233,665 | 8/1993 | Vaughn et al. | 381/98 |
| 5,406,633 | 4/1995 | Miller et al. | 381/68.2 |
| 5,481,617 | 1/1996 | Bjerre | 381/98 |
| 5,530,769 | 6/1996 | Saitoh | 381/103 |

*Primary Examiner*—Curtis Kuntz
*Assistant Examiner*—Vivian Chang
*Attorney, Agent, or Firm*—Harry M. Weiss; Jeffrey D. Moy; Harry M. Weiss & Associates, P.C.

[57] ABSTRACT

In one mode of operation, a signal representation of sound is provided to an audio filter that has transmission characteristics that are controlled by a microprocessor. The output of the audio filter is provided to similar left and right ear and a bone conduction processing circuits. Each of the processing circuits has an equalization filter that has transmission characteristics that are determined by the microprocessor. The outputs of the left and right ear and bone conduction processing circuits are connected to a left earphone, a right earphone and a bone transducer, respectively. The outputs of the processing circuits are in accordance with a program stored in a memory unit and are in accordance with plurality of procedures for assessment and training of a person's listening ability. In another mode of operation, a voltage to frequency converter generates a voltage having a frequency in accordance with signals provided by a microprocessor. The output of the converter is connected through an attack/decay filter to the input of the processing circuits.

16 Claims, 1 Drawing Sheet

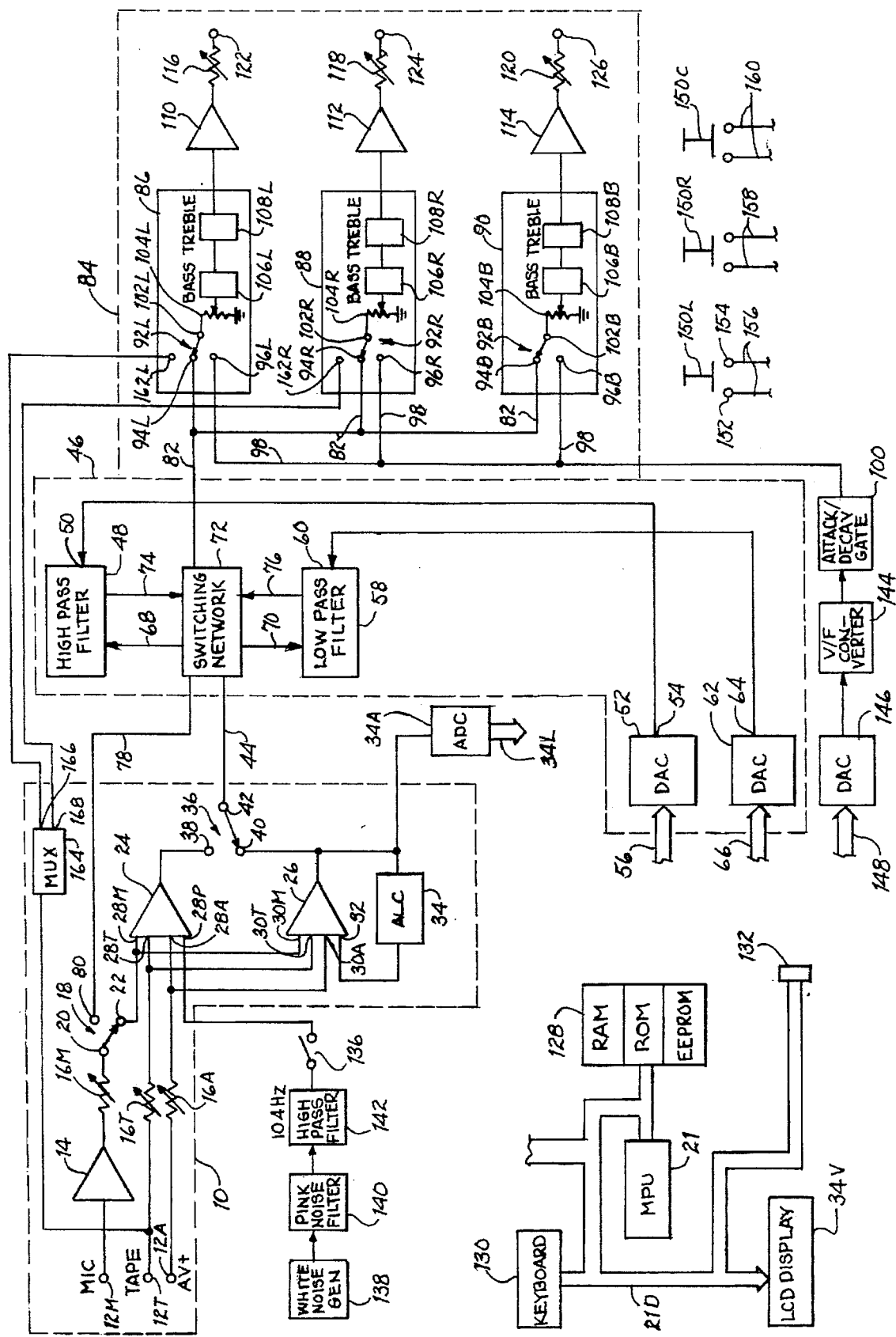

APPARATUS AND METHODS FOR AUDITORY CONDITIONING

BACKGROUND OF THE INVENTION

1. Field of Invention

This invention is in the field of apparatus and methods for conditioning a person's auditory/vestibular system and, more particularly, is an apparatus for enhancing sound provided to the auditory/vestibular system of a person via air and bone conduction and methods for using the apparatus to condition the auditory/vestibular system of a person that has a listening disorder.

2. Description of the Prior Art

There are seven principal aspects of listening which are given as follows:

A first aspect of listening is defined as a motivated functional ability of a person to attend ("tune in") some sound and reject ("tune out") other sound.

A second aspect of listening is defined as an ability of the person to discriminate between sounds having differing frequencies within an audio frequency range.

A third aspect of listening is defined as an ability of the person to determine the spatial origin of a sound.

A fourth aspect of listening is defined as an ability to make a timely response to sonic stimuli and an ability to make a timely response to a change in sonic stimuli.

A fifth aspect of listening relates to an ability of the person to control their speech by establishing a lateralization of sound to the person's right ear. Lateralization is explained hereinafter.

A sixth aspect of listening relates to an ability of a person to derive meaning or recognition of incoming sound signals such as from tonal type or lexical type signals.

A seventh aspect of listening relates to an ability of a person to be sensitive to memories stored in a person's body which are activated by a sonic stimulation.

Correspondingly, there are four aspects of vestibular functioning which are as follows:

A first aspect is the analysis of movement of the body such that erect posture and spatial balance are maintained.

A second aspect is the ability to coordinate the signals from throughout the body.

A third aspect is the ability to respond in a desired way to one's incoming motor and sensory signals in a timely manner.

A fourth aspect is to integrate sensory and neurophysiological information such that complex behaviors such as reading aloud without error is accomplished in a timely manner.

Sound is heard because it passes through air to a person's ears (known as air conduction) and through bones near the ears (known as bone conduction). Although the person's hearing may be substantially unimpaired by either sensory neural loss, conduction loss or osteoporosis, for example, the person may have a defective ability to listen. The defective listening ability has been associated with many disorders (referred to as listening disorders) some of which are described hereinafter.

A training procedure for dealing with a listening disorder has been suggested only within the past forty years. There are many disorders which have yet to be ascribed to the defective ability to listen. There are some listening disorders for which auditory conditioning is a known successful training procedure. There are other listening disorders for which auditory conditioning is not a known successful training procedure.

When the person does not have a sensory neural loss, auditory conditioning is used to deal with an inability to discriminate between sounds of the differing frequencies and to treat insensitivity to sound. The insensitivity may cause the person to experience a lack of motivation, lack of creativity and lack of energy. Typically, the insensitivity has a psychological and/or a neurophysiological basis.

Auditory conditioning is additionally used to deal with the person's inability to tune out or to comfortably perceive sound at known frequencies within the audio frequency range, thereby causing a two open reception or a hypersensitivity to sound at the known frequencies. Typically, the hypersensitivity has a psychological and/or neurophysiological basis.

When the person has an inability to attend and concentrate, it may be a manifestation of a reduced ability to listen to sound transmitted via air conduction (when compared to the ability to listen via bone conduction) that can be dealt with by auditory conditioning. Typically, the inability to attend and concentrate has a psychological and/or neurophysiological basis.

A speech articulation and/or fluency defect is often related to the person's inability to perceive and distinguish sound signals clearly and to efficiency use the neurological pathways to a hearing center on the left side of a person's brain (left side hearing center) from the person's ears. The left side hearing center controls the person's speech organs.

The most efficient neurological pathway to the left side hearing center is from the person's right ear; a neurological pathway from the person's left ear is less efficient. Through a process known as lateralization, auditory conditioning is used to cause a dominance of the neurological pathway from the right ear to the left side hearing center, known as right ear dominance. Most people (and practically all singers) have right ear dominance.

A listening temporal spatial disorder manifests itself as a difficulty in determining the spatial origin of a source of sound. Auditory conditioning has been used to deal with the temporal spatial disorder.

Reading aloud is one of the most important human skills and a significant basis for learning. When the person is unable to read aloud, she is said to have a listening reading aloud (LRA) disorder.

The LRA disorder is a manifestation of the person's inability to integrate motor signals from their vestibular system and/or sound signals from the cochlea may be related to an inability to integrate aural, visual, vocal functions and a plethora of other functions. The inability to integrate is caused by visual sensations being processed by the person's brain at one rate and aural sensations being processed at another rate. The inability to integrate may additionally effect the person's reading and posture.

The LRA disorder may produce what is known as dyslexia. Dyslexia is a disorder whereby the person omits words and letters, adds words and reverses the order of words in a text that she reads aloud. Additionally, the LRA disorder may produce an inability to distinguish sounds of different frequencies. The LRA disorder has been dealt with by auditory conditioning.

When the person either consciously or subconsciously dislikes the sound of their own voice, they have what is known as a vocal dislike listening disorder. There are aspects of the vocal dislike listening disorder that have not been dealt with by auditory conditioning.

It should be understood that every muscle of the person's body is neurologically connected to the person's vestibular system. Because of the connection, the condition of the person's vestibular system bears upon all aspects of the person's motor control, such as the person's posture and the ability of the person's body to work efficiently. Auditory conditioning has been used to deal with motor control problems.

A listening disorder is dealt with during a minimum training period of two weeks. During the training period, there is typically intensive conditioning over sequential days. This is followed by breaks for integration of changes in the conditioning, followed by additional conditioning.

SUMMARY OF THE INVENTION

An object of the present invention is to provide an apparatus and method that are used for assessing and dealing with a listening disorder.

Another object of the present invention is to provide an apparatus and method for assessing and treating a listening disorder where the apparatus is optionally linked to a computer.

Another object of the present invention is to provide an apparatus and method for assessing a person's ability to attend auditorially.

Another object of the present invention is to provide an apparatus and method for selecting one of a plurality of calibration systems for reporting aspects of a person's perception of sound.

Another object of the present invention is to provide an apparatus and method for selectively transmitting sound to the auditory system of a person via air and bone conduction.

Another object of the present invention is to provide an apparatus and method for filtering a signal representation of sound that is provided to an earphone and/or a bone transducer.

Another object of the present invention is to provide an apparatus and method for transmitting a sound to a person via bone conduction and air conduction with a known time delay therebetween.

Another object of the present invention is to provide an apparatus and method for optionally compressing the volume of sound transmitted to a person during auditory conditioning.

Another object of the present invention is to provide an apparatus and a method for equalizing a signal representation of sound where the equalization is changed in response to the sound having a selected volume.

Another object of the present invention is to provide an apparatus and method for assessing the degree of a person's right or left ear dominance.

Another object of the present invention is to provide an apparatus and method for assessing the variance of a person's auditory processing state from their optimal auditory processing state.

Another object of the present invention is to provide a method for assessing a person's ability to locate a source of sound transmitted to the person through either air or bone conduction where the sound is at one of a plurality of frequencies and at one of a plurality of volume levels.

Another object of the present invention is to provide a method for assessing a person's erroneous perception of sonic distortion.

Another object of the present invention is to provide an apparatus and method for assessing a person's time to respond to sound over a volume range that extends from barely audible sound to clearly audible sound.

Another object of the present invention is to provide an apparatus and method that is used by a person to attain their optimal auditory processing state.

Another object of the present invention is to provide an apparatus and method that is used by a person to maintain their optimal auditory processing state.

Another object of the present invention is to provide an apparatus and method for conditioning a person to have a desired time delay between air and bone conduction of sound to their auditory system and muscles associated therewith.

Another object of the present invention is to provide an apparatus and method for dealing with an undesired imbalance of perception of sound via a person's left and right ears.

Another object of the present invention is to provide an apparatus and method for enhancing a person's creative ability.

Another objective of the present invention is to provide an apparatus and method that enhances a person's ability either to sing or to play a musical instrument.

Another object of the present invention is to provide an apparatus and method for dealing with a person's inability to perceive differences and similarities in frequencies of sound.

Another object of the present invention is to provide an apparatus and method for dealing with a hypersensitivity related to a person's auditory system.

Another object of the present invention is to provide an apparatus and method for dealing with a depressed mental state of a person caused by either a physical or an emotional trauma, illness or genetic factors.

Another object of the present invention is to provide an apparatus and method for dealing with a vestibular disorder that adversely affects either a person's sense of spatial orientation, balance, the efficiency of their posture or motor control.

Another object of the present invention is to provide an apparatus and method for dealing with a vocal articulation disorder of a person caused by either a physical or an emotional trauma, illness, developmental delay or genetic factors.

Another object of the present invention is to provide an apparatus and method for dealing with a speech disorder of a person caused by either a physical or an emotional trauma, illness, developmental delay or genetic factors.

Another object of the present invention is to provide an apparatus and method for dealing with an attention deficit disorder of a person caused by either a physical or an emotional trauma, illness, developmental delay or genetic factors.

Another object of the present invention is to provide an apparatus and method for dealing with a listening disorder by conditioning a person's auditory system and then integrating the person's listening ability with their ability to speak, read and write.

Another object of the present invention is to provide an apparatus and method for influencing a person's neurovegetative balance.

Another object of the present invention is to provide an apparatus and method for dealing with a person's inability to perceive sounds over a substantial portion of the audio frequency range.

Another object of the present invention is to provide an apparatus and method for dealing with a person's inability to tune out undesired sound and tune in desired sound by conditioning a person's auditory system.

Another object of the present invention is to provide an apparatus and method for dealing with a person's discomfort to changes in their environment and their resistance to these changes.

Another object of the present invention is to provide an apparatus and method for dealing with a person's erroneously perceived sonic distortion.

Another object of the present invention is to provide an apparatus and method for dealing with a disorder caused by an inefficient neurological pathway to a hearing center in the left side of a person's brain.

BRIEF DESCRIPTION OF THE PREFERRED EMBODIMENT

According to a sound enhancement aspect of the present invention, one or more audio signal sources are adapted for connection to the input of a summing amplifier. The output of the summing amplifier is connected to a filter that has transmission characteristics that are controlled by a microprocessor. The output of the variable filter is connected to the input of a processing circuit that includes an equalization filter that has a frequency response that is controlled by the microprocessor. The output of the processing circuit is adapted for connection to a transducer that provides sound to a person's auditory system.

According to a hearing tester aspect of the present invention, in a first mode of operation, pink noise is fed through a high pass filter to the summing amplifier. In response to signals derived from the output of the microprocessor, the variable filter has low pass transmission characteristics, whereby the composite characteristic of the variable filter and the high pass filter is that of a band pass filter. In a second mode of operation, a voltage to frequency converter generates a voltage having a frequency in accordance with signals provided by the microprocessor. The output of the converter is connected through an attack/decay filter to the input of the processing circuit. In a third mode of operation, sound derived from a two channel tape is binaurally provided via earphones.

According to a threshold level assessment method of the present invention, sound at a selected frequency and amplitude is provided to a person's auditory system alternatively via an earphone or a bone transducer. The person indicates when the sound is heard thereby indicating a delay between the start of the sound and its perception and the perceived direction of its origin.

According to a tone discrimination assessment method of the present invention, a clearly audible sound at a first frequency is provided to a person's auditory system alternatively via an earphone or a bone transducer. Thereafter, a clearly audible sound of a second frequency is provided to the person. The person indicates when the sound of the second frequency is perceived and whether it is perceived as being higher, lower or the same as the first frequency.

According to a left ear/right ear dominance assessment method of the present invention, a person speaks through a microphone to generate sound that is provided to the person's left and right ears. Initially, the sound levels provided to the ears are substantially equal. The person indicates whether sound is perceived more strongly by the left ear or the right ear, thereby determining either a right ear or a left ear dominance. When the dominance is determined, the sound level provided to the non-dominant ear is increased until it is perceived more strongly by the non-dominant ear.

According to a method of treating a hypersensitivity of a person to sound at a known frequency, the person listens to a sonic composition where the volume of sound at the known frequency is reduced. When the person can read aloud, the person listens to a filtered replication of their own voice, frequently accompanied by background music, where the volume of sound at the known frequency is reduced. The attenuation of the filtered replication, as well as the amount of filtering, is adjusted during the training to gradually increase sound at the hypersensitivity frequency.

According to a method of treating an inability of a person to perceive differences and similarities in the frequencies of sound, the person listens to a sonic composition that is filtered to emphasize sound within a frequency range of less easily perceived frequencies.

According to a method of treating a vestibular disorder that effects either a person's sense of spatial orientation, balance, the efficiency of their posture or motor control, the person listens to a sonic composition with rhythm and pattern that is likely to motivate the person. The sonic composition has an amplitude compression and is filtered to emphasize its lower audio frequency range.

According to a method of treating a person's depressed mental state, the person listens to a sonic composition that is filtered to emphasize its upper frequency range.

According to a method of treating an attention deficit disorder and dyslexia, the person listens to a sonic composition via air and bone conduction. Pseudo random changes are made in filtering of the bone conduction. A change in the filtering of the bone conduction is followed by a change in the filtering of the air conduction, with the delay between the changes being reduced as the training progresses.

Apparatus and methods according to the invention are economically used to implement training procedures for listening disorders.

Other objects, features and advantages of the present invention should be apparent from the following description of the preferred embodiment as illustrated in the accompanying drawing.

BRIEF DESCRIPTION OF THE DRAWING

The sole FIGURE herein is a schematic block diagram of apparatus in accordance with the preferred embodiment of the present invention.

DESCRIPTION OF THE PREFERRED EMBODIMENT

Diagnostic and Training Apparatus

The apparatus of the present invention is primarily for enhancing a signal representation of sound for the purpose of conditioning a person's auditory system. The apparatus is additionally used for testing hearing. The methods of the present invention are for assessing listening ability and for treating listening disorders.

As shown in the drawing, an audio input section 10 is comprised of a microphone input terminal 12M connected to an amplifier 14 at an input thereof. When a microphone audio voltage is provided by a microphone (not shown), it is received at the input of amplifier 14 via terminal 12M. Amplifier 14 has a high input impedance, thereby making it suitable to receive the microphone voltage. Amplifier 14 provides an amplified microphone voltage at its output.

The output of amplifier 14 is connected through a variable input attenuator 16M to a solid state switch 18 at a pole 20 thereof. Amplifier 14 has a low output impedance, thereby making it suitable for providing the amplified microphone voltage to attenuator 16M. In response to the amplified microphone voltage, attenuator 16M provides an attenuated microphone voltage. Attenuation provided by attenuator 16M is controlled by signals derived from the output of a microprocessor 21.

Switch 18 has a contact 22 that is connected to summing amplifiers 24, 26 at inputs 28M, 30M, respectively. Accordingly, when switch 18 is thrown to provide an ohmic connection between pole 20 and contact 22, the attenuated microphone voltage is applied through switch 18 to inputs 28M, 30M. Switch 18 is thrown in response to signals derived from the output of microprocessor 21.

A tape input terminal 12T is connected through an attenuator 16T to summing amplifiers 24, 26 at inputs 28T, 30T respectively. Attenuator 16T is similar to attenuator 16M described hereinbefore.

When a tape audio voltage is provided by a tape player (not shown) via terminal 12T to attenuator 16T, it is attenuated whereby an attenuated tape voltage is applied to inputs 28T, 30T.

An auxiliary input terminal 12A is connected through an attenuator 16A to summing amplifiers 24, 26 at inputs 28A, 30A respectively. Attenuator 16A is similar to attenuators 16T, 16M.

When an auxiliary audio voltage is provided by any suitable source via terminal 12A to attenuator 16A, it is attenuated, whereby an attenuated auxiliary voltage is applied to inputs 28A, 30A. From the description given hereinbefore, one or more sources of an audio voltage may be connected to section 10.

Summing amplifiers 24, 26 are of a type that provide an output voltage having an amplitude proportional to the sum of the amplitudes of voltages respectively applied to its inputs. Accordingly, summing amplifier 24 provides an output voltage having an amplitude proportional to the sum of voltages provided by sources connected to section 10.

As explained hereinafter, a feedback connection of an automatic level control circuit causes an amplitude compression of the output voltage provided by summing amplifier 26. Summing amplifiers are well known to those skilled in the art.

The output of summing amplifier 26 is connected to an input 32 thereof through an automatic level control circuit (ALC) 34, whereby ALC 34 is a feedback path from the output of summing amplifier 26 to input 32. ALC 34 is a nonlinear circuit having a gain that is directly related to the amplitude of a voltage applied thereto.

The output of ALC 34 is of a polarity that causes ALC 34 and summing amplifier 26 combine to form an amplifier stage having a gain that is inversely related to the amplitude of a compressed gain voltage provided at the output of summing amplifier 26. In other words, the amplifier stage provides the amplitude compression referred to hereinbefore. The output of summing amplifier 26 is connected to an analog to digital converter (ADC) 34A at an analog input thereof.

The compressed gain voltage is digitized by ADC 34A to provide a digital signal representation of the compressed gain voltage on a plurality of signal lines 34L. The signal representation of the compressed gain voltage is provided to microprocessor 21. In response to the signal representation of the compressed gain voltage, microprocessor 21 provides a software representation of the compressed gain voltage.

Microprocessor 21 is connected through a data bus 21D to a liquid crystal display (LCD) 34V. Microprocessor 21 may be controlled to cause LCD 34V to display an image of a VU meter whereon a visual indication of the compressed gain voltage is provided. In a similar manner, LCD 34V provides status information relating to other aspects of the apparatus. LCD displays are well known to those skilled in the art.

Microprocessor 21 causes a comparison between the software representation of the compressed gain voltage and a software representation of a selected threshold voltage. Because of the compressed gain, the threshold voltage is within a reduced range. The use of the comparison with the threshold voltage is more fully explained hereinafter.

The outputs of summing amplifiers 24, 26 are connected to a solid state selector switch 36 at contacts 38, 40, respectively. A pole 42 of switch 36 is connected through a signal line 44 to a variable transmission filter section 46. Additionally, contact 18 is connected through a signal line 78 to section 46.

Switch 36 is thrown to provide an ohmic connection between pole 42 and either contact 38 or contact 40 in response to signals derived from the output of microprocessor 21. When the apparatus is used for enhancing sound, typically switch 36 is thrown to provide the ohmic connection between pole 42 and contact 38, whereby the output of summing amplifier 24 is provided to section 46. The ohmic connection between pole 42 and contact 38 is provided in response to an amplifier 24 selection signal derived from the output of microprocessor 21.

It has been empirically determined that it is often desirable for switch 36 to be thrown to provide the ohmic connection between pole 42 and contact 40, whereby the gain compressed voltage is provided to section 46. Sound provided in response to the gain compressed voltage is said to be "denser" than sound provided in response to the output of summing amplifier 24. The ohmic connection between pole 42 and contact 40 is provided in response to an amplifier 26 selection signal derived from the output of microprocessor 21.

Section 46 is comprised of a high pass filter 48. Within filter 48 are a plurality of variable transconductance amplifiers that are respective filter resistive elements. A low frequency cutoff of filter 48 is determined by the values of its resistive elements. The resistive elements of filter 48 have values in accordance with the amplitude of a low frequency cutoff voltage applied to its variable transconductance amplifiers via a cutoff frequency input 50 of filter 48.

Input 50 is connected to a digital to analog converter (DAC) 52 at an output 54 thereof. The input of DAC 52 is connected to a plurality of signal lines 56 where a digital signal representation of a desired low frequency cutoff of filter 48 is applied. The signal representation of the low frequency cutoff is derived from the output of microprocessor 21.

In response to the signal representation of the low frequency cutoff, DAC 52 provides the low frequency cutoff voltage. Digital to analog converters and variable transconductance amplifiers are well known to those skilled in the art.

Section 46 is additionally comprised of a low pass filter 58. Within filter 58 are a plurality of variable transconductance amplifiers that are respective filter resistive elements. A high frequency cutoff of filter 58 is determined by the values of its resistive elements. Similar to filter 48, the resistive elements of filter 58 have values in accordance with the amplitude of a high frequency cutoff voltage applied to its variable transconductance amplifiers via a cutoff frequency input 60 of filter 58.

Input 60 is connected to a digital to analog converter (DAC) 62 at an output 64 thereof. DAC 62 is similar to DAC 52 referred to hereinbefore.

The input of DAC 62 is connected to a plurality of signal lines 66 where a digital signal representation of a desired high frequency cutoff of filter 58 is applied. The signal representation of the high frequency cutoff is derived from the output of microprocessor 21. In response to the signal representation of the high frequency cutoff, DAC 62 provides the high frequency cutoff voltage.

Signal inputs of filters 48, 58 are respectively connected through signal lines 68, 70 to a switching network 72. Signal outputs of filters 48, 58 are respectively connected through signal lines 74, 76 to switching network 72.

Switching network 72 has one input connected to line 44 and another input connected through a signal line 78 to a contact 80 of switch 18. A filter section output voltage is provided through a signal line 82 by switching network 72 to an output section 84. Switching network 72 is made from solid state analog switches of any suitable type.

As explained hereinafter, switching network 72 is operable to alternatively configure filter section 46 as a high pass filter, a low pass filter, a band pass filter and a band rejection filter. Additionally, when switch 18 is thrown to cause an ohmic connection between pole 20 and contact 80, the attenuated microphone voltage passes through switch 18 to the output of switching network 72. The operation of switching network 72 is in response to signals derived from the output of microprocessor 21.

When section 46 is configured as a high pass filter, switching network 72 provides an ohmic connection between signal lines 44, 68 and between signal lines 74, 82. Correspondingly, when section 46 is configured as a low pass filter, switching network 72 provides an ohmic connection between signal lines 44, 70 and between signal lines 76, 82.

When section 46 is configured either as a band pass or a band rejection filter, filters 48, 58 are connected in cascade. More particularly, switching network 72 provides an ohmic connection between signal lines 44, 68, between signal lines 70, 74 and between signal lines 76, 82.

It should be understood that the band pass filter is provided when the low frequency cutoff of filter 48 is less than the high frequency cutoff of filter 58. Conversely, the band rejection filter is provided when the low frequency cutoff of filter 48 is greater than the high frequency cutoff of filter 58. From the explanation given hereinbefore, section 46 is a filter with variable transmission characteristics.

Output section 84, referred to hereinbefore, is comprised of a left ear processing circuit 86, a right ear processing circuit 88 and a bone conduction processing circuit 90. Processing circuits 86, 88, 90 are similar.

Processing circuits 86, 88, 90 include respective solid state selector switches 92L, 92R, 92B that have contacts 94L, 94R, 94B all connected through line 82 to switching network 72. Additionally, contacts 96L, 96R, 96B of switches 92L, 92R, 92B, respectively, are all connected through a signal line 98 to an attack/decay gate 100 which is more fully explained hereinafter.

When the apparatus is used for enhancing sound, switches 92L, 92R, 92B are thrown to provide an ohmic connection contacts 94L, 94R, 94B and poles 102L, 102R, 102B of switches 92L, 92R, 92B, respectively. Switches 92L, 92R, 92B are thrown in response to a filter section selection signal derived from the output of microprocessor 21.

Poles 102L, 102R, 102B are connected to variable attenuators 104L, 104R, 104B, respectively, at their inputs. Accordingly, the filter section output voltage is applied to the inputs of attenuators 104L, 104R, 104B via poles 102L, 102R, 102B, respectively.

Attenuators 104L, 104R, 104B have outputs respectively connected to bass circuits 106L, 106R, 106B at their inputs. Outputs of bass circuits 106L, 106R, 106B are respectively connected to treble circuits 108L, 108R, 108B at their inputs. Bass circuit 106L and treble circuit 108L form a left ear equalization filter. Similarly, bass circuit 106R and treble circuit 108R form a right ear equalization filter and bass circuit 106B and treble circuit 108B form a bone conduction equalization filter.

The attenuations of processing circuits 86, 88, 90 are provided by attenuators 104L, 104R, 104B, respectively; bass and treble frequency responses are determined by the equalization filters. Moreover, the attenuations, and the frequency responses of the equalization filters are determined by signals derived from the output of microprocessor 21. For training of a number of listening disorders, it is desirable that the frequency responses of the equalization filters change in response to the software comparison referred to hereinbefore.

It should be understood that the outputs of circuits 108L, 108R, 108B comprise the outputs of processing circuit 86, 88, 90, respectively. The outputs of processing circuits 86, 88, 90 are connected to power amplifiers 110, 112, 114, respectively, at inputs thereof. The outputs of power amplifiers 110, 112, 114 are respectively connected through attenuators 116, 118, 120 to a left ear terminal 122, a right ear terminal 124 and a bone transducer terminal 126. Attenuations provided by attenuators 116, 118, 120 are in response to signals derived from the output of microprocessor 21.

The purpose of attenuators 116, 118, 120 is to control the operating point of power amplifiers 110, 112, 114, respectively. When, for example, a low level signal terminal 122 has an amplitude that is comparable to noise inherently provided by amplifier 110, a signal may be provided at the output of amplifier 110 that is much higher than the inherent noise. When the signal at the output of amplifier 110 is attenuated to provide the low level signal, the inherent noise is attenuated. Therefore, attenuator 116 serves to improve the signal to noise ratio at terminal 122. Correspondingly, attenuators 118, 120 serve to improve the signal to noise ratio at terminals 124, 126.

Terminals 122, 124 are adapted for connection to earphones (not shown). Terminal 126 is adapted for connection to a bone transducer (not shown) that is typically connected behind the right ear of the person.

Microprocessor 21 is connected through data bus 21D to a memory unit 128 comprised of a random access memory (RAM), a read only memory (ROM) and an erasable programmable read only memory (EEPROM). The RAM is used for storage of signal representations of variables, such as a threshold voltage. The ROM is used for storage of a signal representation of a program that determines the operation of the apparatus. The EEPROM is used for a storage of signal representations of calibration values. RAMs, ROMs and EEPROMs are well known to those skilled in the art.

Microprocessor 21 is additionally connected through data bus 21D to a keyboard 130. Inputs, such as the signal representations of the calibration variables, may be entered into the RAM via keyboard 130 and microprocessor 21. Provision is made for operating the apparatus remotely from a personal computer by a connection of microprocessor 21 to a terminal 132 via data bus 21D.

From the description given hereinbefore, an audio voltage may be filtered in accordance with signals derived from the output of a microprocessor to provide the filtered section output voltage. Signal representations of sound to the left and right ears and bone structure of the person is provided via respective processing circuits in response to the filtered section output voltage. The attenuation and frequency responses of the processing circuits is controlled by signals derived from the output of microprocessor 21.

When the apparatus is used to test the hearing of the person, three tests may be performed. In a first test, a solid state switch 136 is closed. Additionally, switch 36 is thrown to cause the ohmic connection between pole 42 and contact 38 in response to the amplifier 24 selection signals. Switches 92L, 92R, 92B are thrown to cause the ohmic connection between contacts 94L, 94R, 94B and poles 102L, 102R, 102B, respectively, in response to the filter section selection signals.

The first test utilizes a white noise generator 138 connected to the input of a pink noise filter 140. White noise generator 138 is of a type that provides a white noise voltage having substantially all frequency components. The amplitude of a white noise component is directly related to its frequency.

Pink noise filter 140 operates on the white noise voltage to provide a pink noise voltage having substantially all frequency components. However, all pink noise components are of substantially equal amplitude.

The output of pink noise filter 140 is connected to the input of a high pass filter 142 that has a low frequency cutoff of 104 hertz. Switch 136, referred to hereinbefore, has a pole connected to the output of filter 142 and a contact connected to an input 28P of summing amplifier 24. Accordingly, the output of filter 142 is connected through switch 136 to input 28P.

First test selection signals, derived from the output of microprocessor 21, cause section 46 to be configured as a low pass filter with a high frequency cutoff of 145 hertz. Since filter 142 and the 145 hertz filter are in cascade, they form a band pass filter that operates on the pink noise voltage.

The output of section 46 is provided through processing circuits 86, 88, 90 to amplifiers 110, 112, 114, respectively, as described hereinbefore. It should be appreciated that section 46 is not used to provide the band pass filter configuration because the variable transconductances cause an instability of filter 48 at frequencies on the order of 100 hertz and lower.

In the second test, switches 92L, 92R, 92B are thrown to cause the ohmic connection between poles 102L, 102R, 102B and contacts 94L, 94R, 94B, respectively, in response to second test selection signals derived from the output of microprocessor 21. Accordingly, the output of attack/decay gate 100 is provided to the inputs of attenuators 104L, 104R, 104B.

Attack/decay gate 100 has an input connected the output of a voltage to frequency converter 144. A digital to analog converter (DAC) 146 is connected to apply a frequency selection voltage to the input of converter 144. DAC 146 is similar to DACs 52, 62.

The input of DAC 146 is connected to a plurality of signal lines 148 where a digital signal representation of a frequency is applied. The signal representation of the frequency is derived from the output of microprocessor 21. In response to the signal representation of the frequency, DAC 146 provides the frequency selection voltage referred to hereinbefore.

Converter 144 provides a voltage having a frequency proportional to the amplitude of a voltage applied to its input. Accordingly, the frequency of the voltage provided at the output of converter 144 is proportional to the frequency selection voltage.

Attack/decay gate 100 gates the output of converter 144 to produce at its output a signal having an attack/decay envelope in conformance with ANSI S6.3 section 9.5.3. The attack/decay envelope is well known to those skilled in the art.

Apparatus for a third test includes a contact 162L of switch 92L connected to a multiplexer 164 at an output 166 thereof. Similarly, a contact 162R is connected to an output 168 of multiplexer 164. The input of multiplexer 164 is connected to terminal 12T.

The third test is performed with contacts 162L, 162R in ohmic contact with poles 102R, 102L, respectively, in response to signals derived from the output of microprocessor 21. Additionally, the output of a two channel tape player is connected to terminal 12T.

The output of the two channel tape player is provided to the input of multiplexer 164 via terminal 12T. In response to the output of the tape player, multiplexer 164 provides a left ear audio signal and a right ear audio signal to contacts 162L, 162R, respectively. Therefore, the left and right ear audio signals are respectively applied to the inputs of the left and right ear signal paths.

The outputs of the left and right ear signal paths are respectively connect to the left and right earphones, respectively, whereby left ear and right ear output signals are respectively provided to the left and right earphones. The third test is commonly known as a binaural test.

Assessment Procedures

A training procedure for dealing with a person's listening disorder is determined by an assessment procedure, whereby the person's ability to listen is assessed. An assessment program stored in memory unit 128 is executed in accordance with one of a plurality of calibration files that are stored in the EEPROM. The files include representations of calibration systems for reporting aspects of a person's perception of sound. Typical calibration systems are the ANSI S3.6, Tomatis, Flat, and the Fletcher/Munson.

In a threshold assessment procedure, the assessment program causes converter 144 to successively provide a tone signal at the frequency of each of a plurality of selected tones that are in a frequency range of 125 hertz to 10,000 hertz. The tone signal is provided through gate 100 to processing circuits 86, 88, 90.

When the threshold level of the person's response to sound via their left ear is being assessed, the assessment program causes attenuator 104L to adjust the tone signal to a selected amplitude. The tone signal is provided to a left ear signal path comprised of processing circuit 86, amplifier 110 and attenuator 116. In response to the tone signal, a left earphone voltage is provided by the output of the left ear signal path to terminal 122. The left earphone voltage is of substantially the same frequency as the tone signal. A left earphone is connected to terminal 122.

The person concurrently indicates the perception of the tone signal and its origin as being on the left by depressing an input response pushbutton 150L. Similarly, the person concurrently indicates the perception of the tone signal and its origin as being on the right or from an intermediate direction by depressing input response pushbuttons 150R, 150C, respectively.

Pushbutton 150L has contacts 152, 154 that are connected through signal lines 156 to microprocessor 21. When pushbutton 150L is depressed, an ohmic connection is established between contacts 152, 154. In a similar manner, switches 150R, 150C have contacts that are connected through signal lines 158, 160, respectively, to microprocessor 21. In response to depressing switches 150L, 150R, 150C, microprocessor 21 causes the letters, L, R, C, respectively, to be displayed on LCD 34V for a known interval of time.

An examiner records a response delay time from the initial transmission of the tone signal at the selected amplitude to the time that one of pushbuttons 150L, 150R, 150C is depressed. The examiner additionally notes the perceived direction of the origin of the tone signal, thereby determining whether the person has a listening direction disorder (referred to as a spatialization disorder). The spatialization disorder is linked to integration abilities that are needed for the person to be able to read aloud. In a similar manner, the examiner notes the response delay time at other amplitude levels.

Similarly, when the threshold level of the person's response to sound via their right ear is being assessed, the assessment program causes attenuator 104R to adjust the tone signal to the selected amplitude.

The tone signal is provided to a right ear signal path comprised of processing circuit 88, amplifier 112 and attenuator 118. In response to the tone signal, a right earphone voltage is provided by the output of the right ear signal path to terminal 124. The right earphone voltage is of substantially the same frequency as the tone signal. A right earphone is connected to terminal 124. A record of response times and a determination of whether the person has a spatialization disorder of the right ear are obtained in a manner similar to that described in connection with the threshold level assessment of the person's left ear.

Correspondingly, when the threshold level of the person's response to sound via bone conduction is being assessed, the assessment program causes attenuator 104B to adjust the tone signal to the selected amplitude. The tone signal is provided to a bone conduction signal path comprised of processing circuit 90, amplifier 114 and attenuator 120. In response to the tone signal, a bone conduction voltage is provided by the output of the bone conduction signal path to terminal 126. The bone conduction voltage is of substantially the same frequency as the tone signal. A bone transducer is connected to terminal 126.

A record of response times and a determination of whether the person has a spatialization disorder for bone conduction to the left ear is obtained with the bone transducer connected behind the left ear. Similarly, a record of response times and a determination of whether the person has a spatialization disorder for bone conduction to the right ear is obtained with the bone transducer connected behind the right ear.

The response time records are typically used to prepare graphs of response time versus frequency, response time versus amplitude and amplitude versus frequency for a selected response time. The graphs are for air conduction of sound to the person's auditory system via her left and right ears and for bone conduction of sound to the person's auditory system.

When a given sample point on an amplitude versus frequency graph is representative of a power level of over ten decibels greater than a power level represented by an adjacent sample point, the given sample point is said to be representative of a less easily perceived frequency of sound. Conversely, when the given sample point is representative of a power level of over ten decibels less than a power level represented by an adjacent sample point, the given sample point is said to be representative of a more easily perceived frequency of sound.

In a tone discrimination assessment procedure for air conducted sound, an assessment is made of the ability of the person to discriminate between the selected tones. Additionally, an assessment is made of an aspect of the person's integration of the discrimination ability with other human skills.

In the tone discrimination procedure, the assessment program causes converter 144 to provide the tone signal at the frequency of the selected tone having the highest frequency through gate 100 to processing circuits 86, 88, 90. When the ability to discriminate via the left ear is being assessed, the tone signal is provided to the left ear signal path with the left earphone connected to terminal 122. Additionally, the assessment program causes an adjustment of attenuator 104L that results in the highest frequency tone being provided to the left ear at a power level that the person regards as comfortable.

When the comfortable power level is established, the assessment program causes converter 144 to change the frequency of the tone signal to that of the selected tone having the second highest frequency. The person responds by depressing pushbutton 150L when the change in frequency is perceived. The elapsed time for the person to respond to the change is noted. Additionally, the person is asked to state whether the change is perceived as being to a higher frequency or to a lower frequency.

In a similar manner, the elapsed time and the person's response is noted as converter 144 provides tone signals at successively lower frequencies. An assessment of the person's ability to discriminate via the right ear is correspondingly made.

In a left ear/right ear dominance assessment procedure, a microphone is connected to terminal 12M. The assessment program causes switch 18 to be thrown to provide an ohmic connection between pole 20 and contact 80. Switches 92L, 92R are thrown to provide an ohmic connection between pole 102L and contact 94L and between pole 102R and contact 94R, respectively. The left and right earphones are respectively connected to terminals 122, 124. The assessment program adjusts attenuators 104L, 104R, 116, 118 to cause the left and right earphones to produce equal sound levels at the earphones in response to a signal on line 82.

The person is asked to speak into the microphone and listen to a replication of their speech via the left and right earphones. The examiner observes whether the person's mouth flexibility and facial muscle use is more prominent on one side of the face than the other. Additionally, the person is asked to depress pushbuttons 150L, 150R to provide an indication on LCD 34V of whether their voice is perceived more strongly by the left ear or right ear, respectively. The prominence on the right side and the stronger perception of sound by the right ear, for example, indicates right ear dominance.

When right ear dominance has been determined, the examiner causes an adjustment of attenuator 104L to increase the sound level at the left earphone. The sound level at the left earphone is increased until the prominence of the person's muscle flexibility and facial muscle use, as well as the depressing of pushbutton 150L, indicates left ear dominance.

Correspondingly, when left ear dominance has been determined, the examiner causes an adjustment of attenuator 104R to increase the sound level at the right earphone. The sound level at the right earphone is increased until the prominence of the person's muscle flexibility and facial muscle use, as well as the depressing of pushbutton 150R, indicates right ear dominance.

The difference in the sound level at the left and right earphones when dominance changes from the left ear to the right ear, and vice versa, is known as a laterality output audio difference. LCD 34V provides a display of the difference in decibels.

Training Procedures

Hypersensitivity

When the given sample point is representative of the more easily perceived sound, the person is said to have a hypersensitivity to sound at a frequency represented by the sample point. A hypersensitivity program causes switching network 72 to configure section 46 as a rejection filter that rejects the hypersensitivity frequency. When there are a band of frequencies of more easily perceived sounds, switching network 72 configures section 46 as a band rejection filter that rejects the band of frequencies.

When section 46 has the desired configuration, the tape player is used to provide a tape audio voltage representation of music, whereby a filtered tape audio voltage is provided by section 46 to the left ear and right ear signal paths. In response to the filtered tape voltage, the left and right earphone voltages are similar to the filtered tape audio voltage. Applicant has found that when the hypersensitive person listens to sound produced in response to the filtered tape voltages during the training period described hereinbefore, the hypersensitivity is reduced.

When the person can read aloud, the microphone is used to provide a signal representation of the person's voice to section 46. In response to the signal representation of the person's voice, a filtered signal representation of the persons voice is provided to the left ear and right ear signal paths. The outputs of the left ear and right ear signal paths causes a filtered replication of the person's voice to be provided via the left and right earphones.

The hypersensitivity program causes an adjustment of attenuators 104L, 104R that results in a gradual increase in volume of the filtered replication. Additionally, the hypersensitivity program causes an adjustment of the equalization filters of processing circuits 86, 88 to gradually emphasize hypersensitivity frequencies.

Because of the neurological connection of the person's vestibular system to all portions of the person's body, hypersensitivity of portions of the person's body, other than the auditory system, may be successfully treated as described hereinbefore.

Perception of Frequency Differences and Similarities

An inability of the person to perceive frequency differences and similarities of sound, referred to as a frequency perception disorder, may manifest itself as a learning disability, speech articulation problem, lack of musical aptitude or a reading problem. More specifically, the assessment procedure will indicate that the person's hearing has a band of less easily perceived frequencies of sound.

The frequency perception disorder is treated by connecting the tape player to terminal 12T. The tape player is used to play tapes of musical selections that are known to be rich in sonic content within the band of less easily perceived frequencies.

A frequency perception disorder program is utilized to configure section 46 to a band pass filter that passes signals within the band of less easily perceived frequencies. In response to the band pass signals, the left and right ear signal paths provide band pass filtered signals to the left and right earphones. Applicant has found that band pass filtered signals cause music to be provided that increases the person's ability to attend to sound at less easily perceived frequencies.

Motor Control and Balance Disorders

When the person has problems with either their sense of spatial orientation, efficiency of their posture, motor control or balance, it is usually due to a vestibular disorder that is dealt with by auditory conditioning. The auditory conditioning causes the person to have a balanced perception of air and bone conducted sound via their left and right ears. Preferably, the tape player is used to provide a signal representation of music with rhythm and pattern that is likely to motivate the person to attend.

A motor control program causes the ohmic connection between pole 42 and contact 40, whereby the amplitude compression feature of the present invention is utilized. The motor control program additionally causes section 46 to be configured as a low pass filter, thereby emphasizing the pattern and rhythm aspects of signals derived from the tape player. In response to the output of section 46, the left and right ear and bone conduction signal paths provide low pass filtered signals to the left and right earphones and the bone transducer. While the person listens via the earphones and the bone transducer, the person may be asked to engage in sensory integration activities, such as performing specific body movements and doing rhythmic exercises.

Depressed Mental State

Applicant and others have found that phenomena such as depression, lack of creativity and low energy level of the person may be related to a lack of cortical stimulation of the brain. The cortical stimulation is believed to be provided by sound having a frequency greater than 3000 hertz, which is in the upper portion of the audio frequency range.

The cortical stimulation is provided by using the tape player to provide a signal representation of music that has a substantial content within an upper range of frequencies greater than 3000 hertz. Additionally, section 46 is configured as a high pass filter that emphasizes the content within the upper frequency range. In response to the output of section 46, the left and right ear and bone conduction signal paths provide high pass filtered signals to the left and right earphones and bone the transducer.

The amplitude comparison explained hereinbefore may be used to alternately emphasize sound in the middle of the audio frequency range and in the upper frequency range. Additionally, the examiner may interactively cause the ohmic connection between pole 22 and contact 40, whereby the amplitude compression is used to provide the denser sound. The person's creativity may be further stimulated by asking them to engage in activities such as an art exercise, a writing exercise or dancing.

Attention Deficit Disorder ("ADD"), Attention Deficit Hyperactivity Disorder ("ADHD") and Dyslexia ADD, ADHD and dyslexia are usually the result of the person being slow to respond to audio stimulation, in particular, rapidly changing sounds. The slow response is caused by the person focusing on her own thoughts instead of the audio stimulation.

To treat ADD, ADHD and dyslexia, the tape player is used to provide a signal representation of music that has characteristics that increase the person's attentiveness to themselves and to audible sound. The musical characteristics are individualized in accordance with characteristics of the person.

The person's attentiveness is further increased by using the software comparison and timing elements associated with microprocessor 21 to cause pseudo random changes in the equalization filters. Usually, the software comparison causes a change in the bone conduction equalization filter and a delayed change in the left and right ear equalization filters.

During the course of ADD/ADHD/dyslexia training, the delay is gradually reduced. Applicants have found that the use of the delayed change conditions the person to have a desired time delay between air and bone conduction of sound to their auditory system and muscles associated therewith.

Further attentiveness and an integration of the person's auditory and vocal abilities are attained by using the tape player to produce a signal representation of a selected sound or a group of words. The person is asked to orally repeat what they hear. Alternatively, the group of words are in writing and the person is asked to read aloud, thereby exercising the person's integration of visual, vocal and auditory abilities. When the person's abilities are integrated, there is a reduced tendency for the person to perceive words or numbers as being reversed, for example.

While the invention has been particularly shown and described with reference to a preferred embodiment thereof, it will be understood by those skilled in the art that changes in form and detail may be made therein without departing from the spirit and scope of the invention.

I claim:

1. Apparatus for enhancing an input signal representation of sound, comprising:
   input means for providing a signal in the audio frequency range in response to said input signal, said input means comprising:
   an amplifier stage having a gain inversely related to the amplitude of said input signal, whereby said amplifier stage provides a compressed gain signal, said amplifier stage comprising:

a summing amplifier of the type that provides an output signal having an amplitude proportional to the sum of the amplitude of signals respectively applied to its inputs, said input signal being applied to a first input of said summing amplifier; and an automatic level control circuit connected to the output of said summing amplifier and to a second input of said summing amplifier said automatic level control circuit having a gain inversely related to the signal provided by said summing amplifier;

an audio filter, connected to said input means, that provides a filtered audio signal, said audio filter having variable transmission characteristics;

output means, connected to said audio filter means, for providing an output signal in response to said filtered audio signal; and control logic means for selecting said transmission characteristics and for causing an attenuation and equalization of said output signal in accordance with a stored program, said control logic means being operable to alternatively cause a coupling of at least one of said input signal and said compressed gain signal to said audio filter.

2. Apparatus according to claim 1 wherein said input means additionally comprises a voltage to frequency converter having its input connected to said control logic means and its output coupled to said output means, said converter providing a tone signal in response to a signal derived from said control logic means.

3. Apparatus according to claim 2 additionally including an attack/decay gate, the output of said converter being coupled through said gate to said output means.

4. Apparatus according to claim 1 wherein said input means includes means for providing a signal representation of pink noise.

5. The apparatus of claim 4 additionally including a band pass filter having a lower cutoff frequency substantially equal to 104 hertz and an upper cutoff frequency substantially equal to 145 hertz, said pink noise signal being applied to the input of said band pass filter.

6. Apparatus according to claim 1 wherein said input means includes a multiplexer that provides a left ear audio signal and a right ear audio signal to said output means in response to a signal provided by a two channel tape player, said output means including means for providing a left ear output signal and a right ear output signal in response to said left and right ear audio signals.

7. Apparatus according to claim 1 additionally comprising a display connected to said control logic means, said display being operable to provide an image of a VU meter that provides a reading representative of the amplitude of the signal provided at the output of said summing amplifier.

8. Apparatus according to claim 1 wherein said audio filter comprises:

a low pass filter;

a high pass filter;

a switching network that is operable to provide an ohmic connection from said input means alternatively to inputs of said high and low pass filters and connect said high and low pass filters in cascade, operation of said switching network being in response to signals provided by said control logic means.

9. Apparatus according to claim 8 wherein said filters include variable transconductance amplifiers that are connected to said control logic means.

10. Apparatus according to claim 1 wherein said output means comprises:

an attenuator that attenuates an applied signal, the amount of attenuation being in accordance with a signal provided by said control logic means; and an equalization filter connected to said attenuator, transmission characteristics of said output filter being determined by signals provided by said control logic means.

11. Apparatus according to claim 1 wherein said output means comprises:

an air conduction attenuator that attenuates an applied signal, the amount of attenuation being in accordance with a signal provided by said control logic means;

a bone conduction attenuator that attenuates an applied signal, the amount of attenuation being in accordance with a signal provided by said control logic means; and an air conduction and a bone conduction equalization filter that are respectively connected to said air and bone conduction attenuators, said equalization filters having transmission characteristics determined by signals provided by said control logic means.

12. Apparatus according to claim 1 wherein said control logic means comprises:

a microprocessor;

a random access memory that stores a signal representation of a variable;

a read only memory that stores said program; and an erasable programmable read only memory that stores a signal representation of a calibration value, all of said memories being connected to said microprocessor.

13. Apparatus according to claim 12 wherein said erasable programmable read only memory stores a signal representation of an ANSI S 3.6 calibration system.

14. Apparatus according to claim 12 wherein said erasable programmable read only memory stores a signal representation of a Tomatis calibration system.

15. Apparatus according to claim 12 wherein said erasable programmable read only memory stores a signal representation of a flat calibration system.

16. Apparatus according to claim 12 wherein said erasable programmable read only memory stores a signal representation of a Fletcher/Munson calibration system.

* * * * *